US010500224B2

(12) United States Patent
Shin et al.

(10) Patent No.: US 10,500,224 B2
(45) Date of Patent: Dec. 10, 2019

(54) MUTUAL PRODRUG COMPRISING SHORT CHAIN FATTY ACIDS AND ZEBULARINE OR 1'-CYANO-CYTARABINE FOR CANCER TREATMENT

(71) Applicant: KAINOS MEDICINE, INC., Gyeonggi-do (KR)

(72) Inventors: Sunmi Shin, Seoul (KR); Hyangmi Kim, Seoul (KR); Su-Sung Oh, Seoul (KR)

(73) Assignee: KAINOS MEDICINE, INC., Gyeonggi-do (KR)

( * ) Notice: Subject to any disclaimer, the term of this patent is extended or adjusted under 35 U.S.C. 154(b) by 0 days.

(21) Appl. No.: 15/029,852

(22) PCT Filed: Nov. 14, 2014

(86) PCT No.: PCT/KR2014/010972
§ 371 (c)(1),
(2) Date: Apr. 15, 2016

(87) PCT Pub. No.: WO2015/072784
PCT Pub. Date: May 21, 2015

(65) Prior Publication Data
US 2016/0228562 A1 Aug. 11, 2016

Related U.S. Application Data

(60) Provisional application No. 61/904,064, filed on Nov. 14, 2013.

(51) Int. Cl.
*A61K 31/7068* (2006.01)
*C07H 19/06* (2006.01)
*C07H 19/067* (2006.01)
*A61K 47/54* (2017.01)

(52) U.S. Cl.
CPC ........ *A61K 31/7068* (2013.01); *A61K 47/542* (2017.08); *C07H 19/06* (2013.01); *C07H 19/067* (2013.01)

(58) Field of Classification Search
None
See application file for complete search history.

(56) References Cited

U.S. PATENT DOCUMENTS 7,166,581 B1 * 1/2007 von Borstel ......... A61K 31/513
514/49
2013/0196941 A1 8/2013 Ahrabi et al. ................ 514/49

FOREIGN PATENT DOCUMENTS

| GB | 1297398 A * 11/1972 | ............. C07H 19/06 |
| JP | 07-109289 4/1995 | ............. C07H 19/06 |
| JP | 2005-508885 4/2005 | ......... A61K 31/7068 |
| WO | WO 2003/012051 2/2003 | |

OTHER PUBLICATIONS

Ben-Kasus, T., Ben-Zvi, Z., Marquez, V. E., Kelley, J. A., & Agbaria, R. (2005). Metabolic activation of zebularine, a novel DNA methylation inhibitor, in human bladder carcinoma cells. Biochemical pharmacology, 70(1), 121-133. (Year: 2005).*
Chhikara, B. S., Mandal, D., & Parang, K. (2010). Synthesis and evaluation of fatty acyl ester derivatives of cytarabine as antileukemia agents. European journal of medicinal chemistry, 45(10), 4601-4608. (Year: 2010).*
Definition of "compound" and "composition" in Grant and Hackh's chemical dictionary, 5th Ed. McGraw Hill. 1987. p. 148. ISBN 0-07-024067-1 (Year: 1987).*
Yoshimura, Y., Kano, F., Miyazaki, S., Ashida, N., Sakata, S., Haraguchi, K., . . . & Miyasaka, T. (1996). Synthesis and biological evaluation of 1'-C-cyano-pyrimidine nucleosides. Nucleosides, Nucleotides & Nucleic Acids, 15(1-3), 305-324. (Year: 1996).*
Office Action from corresponding Japanese Application No. JP 2016-554157, Apr. 25, 2017.
John S. Driscoll, et al., *J. Med. Chem.*, 34(11); 3280-3284 (1991).
European Search Report dated Mar. 17, 2014 in PCT/KR2014/010972.
Battenberg, O., et al., (2011). "Evaluation of α-pyrones and pyrimidines as photoaffinity probes for affinity-based protein profiling". *The Journal of Organic Chemistry* 76(15):6075-6087.
Gish, D., et al., (1971). "Nucleic acids, 11. Synthesis of 5'esters of 1-β-D-arabinofuranosylcytosine possessing antileukemic and immunosuppressive activity". *Journal of Medicinal Chemistry*. 12(14):1159-1162.
Hamamura, E. K., et al., (1976). "Reactions of 2-acyloxyisobutyryl halides with nucleosides. 8.1a synthesis and biological evaluation of some 3-acyl and 3,5-diacyl derivatives of 1-β-D-arabinofuranosylcytosine 1b". *Journal of Medicinal Chemistry. American Chemical Society*, US 5(19):667-674.
Warner, D., et al., (1972). "Nucleic acids, 13. 3'-0- and 2'-0-esters of 1-β-D-arabinofuranosylcytosine as antileukemic and immunosuppressive agents". *Journal of Medicinal Chemistry*. 8(15):790-793.
Yoshimura, Y., et al., (1996). "Synthesis and biological evaluation of 1'~c-cyano-pyrimidine nucleosides". *Nucleosides & Nucleotides, Marcel Dekker Inc, US*, 15(1-3):305-324.
J. M. Bennett, (2003). "Chronic leukemias and lymphomas: biology, pathophysiology, and clinical management" *Leukemia Research*, 27:761.
Billam, M., et al., (2010). "Effects of a novel DNA methyltransferase inhibitor zebularine on human breast cancer cells" *Breast Cancer Research and Treatment*, 120(3): 581-592.
A. C. Burke, et al., (2011). "Elacytarabine—lipid vector technology overcoming drug resistance in acute myeloid leukemia" *Expert Opinion on Investigational Drugs*, 20:1707-1715.

(Continued)

*Primary Examiner* — Dale R Miller
(74) *Attorney, Agent, or Firm* — Harness, Dickey & Pierce, P.L.C.

(57) ABSTRACT

The present invention provides mutual prodrugs comprising anti-cancer nucleosides and short chain fatty acids; methods for production of the mutual prodrugs; methods of treatment comprising administration of the mutual prodrugs; and pharmaceutical compositions comprising the mutual prodrugs. Further, the mutual prodrugs of the present invention can be used as therapeutic agents for the treatment of cancer diseases and conditions.

6 Claims, 5 Drawing Sheets

(56) References Cited

OTHER PUBLICATIONS

B. Ewald, et al., (2008). "Nucleotide analogs: molecular mechanisms signaling cell death" *Oncogene*, 27:6522-6537.
H. Gourdeau, et al., (2001). "Comparative study of a novel nucleoside analogue (troxatyl, troxacitabine, bch-4556) and arac aainst leukemic human tumor xenografts expressing high or low cytidine deaminase activity" *Cancer Chemotherapy and Pharmacology*, 47:236-240.
A. Hamada, et al., (2002). "Clinical pharmacokinetics of cytarabine formulations" *Clinical Pharmacokinetics*, 41:705-718.
A. K. Jain, et al., (2013). "Mutual prodrugs containing bio-cleavable and drug releasable disulfide linkers" *Bioorganic Chemistry*, 49:40-48.
R. W. Johnstone, (2002). "Histone-deacetylase inhibitors: novel drugs for the treatment of cancer" *Nat Rev Drug Discovery*, 1:287-299.
H. M. Kantarjian, (2007). "Therapy for elderly patients with acute myeloid leukemia" *American Cancer Society*, 109(6):1007-1010.
P. A. Marks et al., (2001). "Histone deacetylases and cancer: causes and therapies" *Nat Rev Cancer*, 1:194-202.
T. Ohta, et al., (2004). "Impact of cytidine deaminase activity on intrinsic resistance to cytarabine in carcinoma cells" *Oncology Reports*, 12:1115-1120.
P. P. Pandolfi, (2001). "Transcription therapy for cancer" *Oncogene*, 20: 3116-3127.
PubChem. (2011). SID 126494944 (https://pubchem.ncbi.nlm.nih.gov/summary/summary.cgi?sid=126494944).
PubChem. (2013). SID 162634335 (https://pubchem.ncbi.nlm.nih.gov/summary/summary.cgi?sid=162634335).
Ramos, M.G., et al., (1997). "Oral administration of short-chain fatty acids reduces the intestinal mucositis caused by treatment with ara-c in mice fed commercial or elemental diets." *Nutrition and Cancer* 28(2):212-217.
O. Schiavon, et al., (2004). "PEG-Ara-C conjugates for controlled release" *European Journal of Medicinal Chemistry*, 39:123-133.
H. Yang, et al., (2005). "Antileukemia activity of the combination of 5-aza-2'deoxycytidine with valproic acid" *Leukemia Research*, 29, 739-748,.
International Search Report (ISR) dated Feb. 27, 2015 in PCT/KR2014/010972 published as WO 2015/072784 with English Translation.
Yang, Z., (2008) "Epigenetic Mechanisms and Therapy of Turnorigenesis.", Sun Yat-Sen University (Natural Sciences, Medicine), *Journal of the Graduates*, 29(4):13-20, with English Abstract.
Chinese Office Action, dated Mar. 27, 2019 issued in Chinese Application No. 201480060553_4.

\* cited by examiner

MUTUAL PRODRUG COMPRISING SHORT CHAIN FATTY ACIDS AND ZEBULARINE OR 1'-CYANO-CYTARABINE FOR CANCER TREATMENT

CROSS-REFERENCE TO RELATED APPLICATIONS

This application is a national phase application of PCT Application No. PCT/KR2014/010972, filed on Nov. 14, 2014, which claims the benefit and priority of U.S. Provisional Application No. 61/904,064, filed Nov. 14, 2013. The entire disclosures of the applications identified in this paragraph are incorporated herein by reference.

FIELD OF THE INVENTION

The present invention relates to a mutual prodrug compound comprising anti-cancer nucleosides and short chain fatty acids (SCFAs) as histone deacetylase inhibitors (HDACIs); a method of preparation thereof; a pharmaceutical composition comprising the same; and a method for preventing or treating a disease, disorder, or condition modulated by anti-cancer nucleosides and histone deacetylase inhibitors.

BACKGROUND OF THE INVENTION

Anti-cancer nucleosides are grouped as antimetabolites, hypomethylating agents or others depending on their mechanism of action. They are typically analogs of natural nucleosides of cytidine, adenosine, guanosine and thymidine (B. Ewald, et al., *Oncogene,* 2008, 27:6522-6537).

For example, cytarabine (hereinafter, referred to as "Ara-C") is a cytosine nucleoside analog and inhibitor of DNA polymerase. It can prevent DNA synthesis, be also incorporated into the DNA and interfere with DNA replication. Currently, Ara-C is mainly used for the treatment of acute leukemia. However, Ara-C has no effect on the majority of solid tumors. This is due to the fact that solid tumors have high level of cytidine deaminase converting the Ara-C into inactive ara-uridine (T. Ohta, et al., *Oncology Reports,* 2004, 12:1115-1120). Oral absorption rate of Ara-C is low, less than 20%, and clearance rate is high, which prohibits the oral dosing (O. Schiavon, et al., *European Journal of Medicinal Chemistry,* 2004, 39:123-133). Instead, it is prescribed as continuous intravenous infusion. Many different types of prodrugs and derivatives have been developed and tested clinically (A. Hamada, et al., *Clinical pharmacokinetics,* 2002, 41:705-716). Lipid-modified Ara-C, called elacytarabine, showed much improved preclinical efficacy in terms of delivery and potency (A. C. Burke, et al., *Expert Opinion on Investigational Drugs,* 2011, 20:1707-1715). However, it failed to show the clinical efficacy. A cytidine deaminase-resistant analog BCH-4556 (H. Gourdeau, et al., *Cancer Chemotherapy and Pharmacology,* 2001, 47:236-240) showed a higher potency than Ara-C, but failed to show the desired efficacy in clinical study.

In order to improve the efficacy of Ara-C, patients are generally treated with Ara-C combined with other drugs, such as, daunorubicin, all-trans retinoic acid, arsenic trioxide, pirarubicin, etoposide, cyclophosphamide and fludarabine. Ara-C has side effects such as bone marrow suppression, gastrointestinal side reaction. A small number of patients may have abnormal liver function, fever, rash and other side effects (J. M. Bennett, *Leukemia Research,* 2003, 27:761; and H. M. Kantarjian, *Cancer,* 2007, 109:1007-1010).

Zebularine is known as a DNA methyltransferase (DNMT) inhibitor, hypomethylating agent, or a demethylating agent. DNA methyltransferases transfer methyl groups from the methyl donor S-adenosyl methionine (SAM) to cytosine of a CpG islands on DNA molecule. Several biological functions for the methylated bases in DNA, including regulation in gene activity, cell differentiation, tumorigenesis, X-chromosome inactivation, genomic imprinting and other major biological processes have been reported (Razin and Riggs, eds. in DNA Methylation Biochemistry and Biological Significance, Springer-Verlag, New York, 1984).

Short chain fatty acids including butyric acid, isobutyric acid, valeric acid, propionic acid, phenylbutyric acid, and its derivative valproic acid are known to be histone deacetylases inhibitors (HDACIs), and affect cell proliferation, gene expression and differentiation.

Histone deacetylases (HDACs) are a group of enzymes responsible for deacetylation of histones and nonhistone proteins. Lysine acetylation, i.e., the transfer of an acetyl moiety from acetyl-coenzyme A to the ε-amino group of a specific lysine residue, is one of the major forms of post-translational modifications of histones, and has been correlated with transcription, chromatin assembly, and DNA repair (Marks et al., *Nat Rev Cancer,* 1:194-202, 2001).

Aberrant acetylation of histone tails, emerging from either HAT (histone acetyl transferases) mutation or abnormal recruitment of HDACs, is known to be associated with carcinogenesis (P. P. Pandolfi, *Oncogene,* 20: 3116-3127, 2001). In various cases, altered HAT or HDAC activity has been identified in a variety of cancers. HDAC inhibitors (HDACIs) are potent inducers of histone acetylation, cell growth arrest, and differentiation and apoptosis of several cell lines. They constitute a novel class of chemotherapeutic agents initially identified by their ability to reverse the malignant phenotype of transformed cells. They activate differentiation programs, inhibit cell cycle, and induce apoptosis in a wide range of tumor-derived cell lines, and thereby blocking angiogenesis and stimulating the immune system in vivo (P. A. Marks et al., *Nat Rev Cancer* 2001, 1:194-202; and R. W. Johnstone, *Nat Rev Drug Discovery* 2002, 1:287-299).

Combination therapy could give an additive or synergistic effect on anti-cancer treatment in various trials. In particular, combinations of DNA hypomethylating agents with histone deacetylase inhibitors were effective on various cancers. For example, DAC is a widely used anti-leukemic agent, and its effects were greatly improved when combined with valproic acid tested on MOLT-4 and HL-60 leukemic cell lines (H. Yang, et al., *Leukemia Research,* 29, 739-748, 2005). The synergistic effect was correlated with DNA demethylation and histone acetylation and with reactivation of the tumor suppressor genes p21CIP and p57KIP2.

A mutual prodrug (hybrid drug, MP) consists of two pharmacologically active agents coupled together so that each acts as a promoiety for the other agent and vice versa. Constituent drugs can be covalently coupled either directly or via a suitable linker (A. K. Jain, et al., *Bioorganic Chemistry,* 2013, 49:40-48). Mutual prodrugs are particularly useful for two or more constituents with potential synergistic or additive effects but difficult to be formulated in a combination pill. When two synergistic agents are administered individually but simultaneously, they will be transported to the site of action with different efficiencies.

However, it is desirable to have the two agents reach a site simultaneously. The mutual prodrug strategy may be used to resolve the problem mentioned above.

Accordingly, there has been a continued need to develop a novel mutual prodrug compound that has improved growth inhibitory activity and exhibits pharmacokinetic properties of drug delivery.

SUMMARY OF THE INVENTION

Accordingly, it is an object of the present invention to provide mutual prodrug compounds that might exert stronger anti-proliferative activity in cancer cells.

It is another object of the present invention to provide a pharmaceutical composition comprising said mutual prodrugs as an active ingredient.

It is a further object of the present invention to provide a method for preventing or treating a disease, disorder, or condition modulated by anti-cancer nucleosides and histone deacetylase inhibitors.

In accordance with one aspect of the present invention, there is provided a mutual prodrug compound comprising a nucleoside of Zebularine represented by formula (I) or 1'-cyano-cytarabine represented by formula (II) linked to one or more short chain fatty acids (SCFAs) or a derivative thereof:

In accordance with another aspect of the present invention, there is provided a pharmaceutical composition for preventing or treating a disease, disorder, or condition modulated by anti-cancer nucleosides and histone deacetylase inhibitors comprising the mutual prodrug compound as an active ingredient, and a pharmaceutically acceptable carrier or an excipient.

In accordance with a further aspect of the present invention, there is provided a method for inhibiting the growth of a cancer cell in a subject, which comprises administering a therapeutically effective amount of the mutual prodrug compound to the subject in need thereof.

In accordance with a still further aspect of the present invention, there is provided a method for preventing or treating a disease, disorder, or condition modulated by anti-cancer nucleosides and histone deacetylase inhibitors in a subject, which comprises administering a therapeutically effective amount of the mutual prodrug compound to the subject in need thereof.

The mutual prodrug compounds of the present invention surprisingly may be more potent than the anti-cancer nucleosides alone and SCFAs (or derivatives) alone in vitro and in vivo. The mutual prodrug compounds of the present invention may be advantageous in terms of pharmacology, pharmacokinetics and toxicology than the anti-cancer nucleosides alone and SCFAs (or derivatives) alone. Also, the mutual prodrug compounds of the present invention may exhibit significant pharmacokinetic properties of drug delivery with an improved efficacy, and overcome low bioavailability of each compound.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The present invention provides a mutual prodrug compound comprising a nucleoside of Zebularine represented by formula (I) or 1'-cyano-cytarabine represented by formula (II) linked to one or more short chain fatty acids (SCFAs) or a derivative thereof:

In the mutual prodrug, zebularine represented by formula (I) and 1'-cyano-cytarabine represented by formula (II), as adenosine analogs, are anti-cancer nucleosides. The compound of formula (I) or (II) is linked to one or more short chain fatty acids (SCFAs) or a derivative thereof.

The SCFAs linked to the nucleoside of formula (I) or (II) may be mono-, di-, tri-short chain fatty acids, or a derivative thereof.

The SCFAs may be any known SCFAs and a derivatives in the art. Non-limiting examples of the SCFAs and derivatives to be linked to hydroxyl group in the compounds of the present invention include propionic acid, butyric acid, isobutyric acid, valproic acid, valeric acid, phenylbutyric acid:

The SCFAs is one to three equivalents to the nucleoside of formula (I) or (II).

The SCFAs may be linked at 2' position, 3' position, 5' position, 2' and 3' positions, 2' and 5' positions, 3' and 5' positions, or 2',3' and 5' positions of the nucleoside of formula (I) or (II).

Examples of more preferred mutual prodrug compound according to the present invention are:
1) ((2R,3S,4S,5R)-5-(4-amino-2-oxopyrimidin-1(2H)-yl)-5-cyano-3,4-dihydroxytetrahydrofuran-2-yl)methyl butyrate;
2) ((2R,3S,4R,5R)-3,4-dihydroxy-5-(2-oxopyrimidin-1(2H)-yl)tetrahydrofuran-2-yl)methyl butyrate;
3) (2R,3R,4R,5R)-2-((butyryloxy)methyl)-5-(2-oxopyrimidin-1(2H)-yl)tetrahydrofuran-3,4-diyl dibutyrate; and
4) (2R,3R,4R,5R)-2-((isobutyryloxy)methyl)-5-(2-oxopyrimidin-1(2H)-yl)tetrahydrofuran-3,4-diyl bis(2-methylpropanoate).

The mutual prodrug compounds comprising a nucleoside of formula (I) linked to one or more SCFAs may be prepared by reacting the nucleoside of formula (I) with SCFA anhydride (e.g., butyric anhydride) in a base (e.g., pyridine, 4-dimethylaminopyridine (DMAP), etc).

The mutual prodrug compounds comprising a nucleoside of formula (II), linked to one or more SCFAs may be prepared by salting the nucleoside of formula (II) with acid, followed by a reaction with butyryl chloride in a base (e.g., dimethylacetamide).

The mutual prodrug compounds comprising anti-cancer nucleoside covalently connected to natural SCFAs or derivatives thereof may have synergistic/additive anti-cancer effects with histone deacetylase inhibitory effects of SCFAs (or its derivatives) for inhibiting cell proliferation, cell cycle arrest, apoptosis, and/or cell differentiation.

The mutual prodrug compounds of the present invention may be used in vitro or in vivo to inhibit growth of a cell, to inhibit growth of a cancer cell, or to treat a subject in need thereof.

Further, the present invention provides a pharmaceutical composition for preventing or treating a disease, disorder, or condition modulated by anti-cancer nucleosides and histone deacetylase inhibitors comprising the mutual prodrug compound as an active ingredient, and a pharmaceutically acceptable carrier or an excipient.

The disease, disorder, or condition modulated by anti-cancer nucleosides and histone deacetylase inhibitors may be selected from the group consisting of an autoimmune disease, epithelial tumors, melanoma, leukemia, acute promyelocytic leukemia, lymphoma, osteogenic sarcoma, colon cancer, pancreatic cancer, breast cancer, prostate cancer, ovarian cancer, lung cancer and a combination thereof.

In one embodiment of the present invention, the mutual prodrug compound may be formulated in a pharmaceutical composition, comprising one or more of the mutual prodrug compound and a pharmaceutically acceptable carrier or an excipient.

The mutual prodrug compound can be mixed with a pharmaceutically acceptable carrier or an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier, or medium for the mutual prodrug compound. Thus, the pharmaceutical compositions can be in the form of tablets, pills, powers, lozenges, sachets, cachets, elixirs, suspensions, emulsions, solutions, syrups, soft and hard gelatin capsules, and other orally ingestible formulations.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, magnesium carbonate, water, ethanol, propylene glycol, syrup, and methyl cellulose. The formulations can additionally include lubricating agents such as talc, magnesium stearate, and mineral oil; wetting agents; emulsifying and suspending agents; preserving agents such as methyl- and propyl-hydroxybenzoates, sweetening agents; and flavoring agents. The compositions of the present invention can also be formulated so as to provide quick, sustained or delayed release of the novel compound after administration to the patient by employing procedures known in the art.

As used herein, the term "pharmaceutically acceptable carrier" refers to those components in the particular dosage form employed which are considered inert and are typically employed in the pharmaceutical fields to formulate a dosage form containing a particular active compound. This may include without limitation solids, liquids and gases, used to formulate the particular pharmaceutical product. Examples of carriers include diluents, flavoring agents, solubilizers, suspending agents, binders or tablet disintegrating agents, encapsulating materials, penetration enhancers, solvents, emollients, thickeners, and dispersants, sustained release forms, such as matrices, transdermal delivery components, buffers, stabilizers, and the like.

The pharmaceutical composition of the present invention may be formulated in the absence or presence of carriers or excipients that provide a sustained released effect.

The pharmaceutical composition of the present invention may be prepared according to methods known in the art. It is contemplated that administration of such compositions may be via oral, injectable and/or parenteral routes depending upon the needs of the subject. The pharmaceutical composition of the present invention can also be administered by nasal or oral inhalation, oral ingestion, injection (intramuscular, intravenous, and intraperitoneal), transdermally, or other forms of administration.

Aerosol formulations for use in this invention typically include propellants, such as a fluorinated alkane, surfactants and co-solvents and may be filled into aluminum or other conventional aerosol containers which are then closed by a suitable metering valve and pressurized with propellant, producing a metered dose inhaler. Aerosol preparations are typically suitable for nasal or oral inhalation, and may be in powder or solution form, in combination with a compressed gas, typically compressed air. Additionally, aerosols may be useful topically.

Topical preparations useful herein include creams, ointments, solutions, suspensions and the like. These may be formulated to enable one to apply the appropriate dosage topically to the affected area once daily, up to 3-4 times daily as appropriate. Topical sprays may be included herein as well.

Depending upon the particular mutual prodrug selected, transdermal delivery may be an option, which can provide a relatively steady state delivery of the medication. Transdermal delivery typically involves the use of a compound in solution, with an alcoholic vehicle, optionally a penetration enhancer, such as a surfactant and other optional ingredients. Transdermal delivery systems of matrix and reservoir type are examples of suitable transdermal systems. Transdermal delivery differs from conventional topical treatment in that the dosage form delivers a systemic dose of medication to the patient.

The present invention includes a method for inhibiting the growth of a cell using one or more of the mutual prodrug compounds of the present invention. In particular, the present invention provides a method for inhibiting the growth of a cancer cell in a subject, which comprises administering a therapeutically effective amount of the mutual prodrug compound to the subject in need thereof.

Also, the present invention provides a method for preventing or treating a disease, disorder, or condition modulated by anti-cancer nucleosides and histone deacetylase inhibitors in a subject, which comprises administering a therapeutically effective amount of the mutual prodrug to the subject in need thereof.

The disease, disorder, or condition modulated by anti-cancer nucleosides and histone deacetylase inhibitors may be selected from the group consisting of an autoimmune disease, epithelial tumors, melanoma, leukemia, acute promyelocytic leukemia, lymphoma, osteogenic sarcoma, colon cancer, pancreatic cancer, breast cancer, prostate cancer, ovarian cancer, lung cancer and a combination thereof.

Also, the present invention provides a method for preventing or treating cancer using one or more of the mutual prodrug compounds of the present invention. In particular, the present invention includes a method for preventing or treating cancer in a subject in need of treatment, comprising administering one or more of the mutual prodrug compounds of the present invention to a subject.

In embodiments of the method of treating cancer, the cancer includes epithelial tumors, melanoma and leukemia, such as acute promyelocytic leukemia, lymphoma, osteogenic sarcoma, colon cancer, pancreatic cancer, breast cancer, prostate cancer, ovarian cancer, and lung cancer.

Combination therapy includes combining the method of treating cancer as described in the invention and one or more cancer therapeutic methods. The cancer therapeutic methods include surgical therapy, radiation therapy, administering an anticancer agent (including, for example, antineoplastics, novantrone, bicalutamide, esterified estrogens, goserelin, histrelin, leuprolide, nilandron, triptorelin pamoate, docetaxel, taxotere, carboplatin, and cisplatin angiogenesis inhibitors), immunotherapy, antineoplastons, investigational drugs, vaccines, and less conventional therapies (sometimes referred to as novel or innovative therapies, which include, for example, chemoembolization, hormone therapy, local hyperthermia, photodynamic therapy, radiofrequency ablation, stem cell transplantation, and gene therapy).

In embodiments of the method of treating cancer, the one or more mutual prodrug may be administered in combination with other active agents.

Generally, the mutual prodrug compound used in the methods of treatment is administered in an amount which effectively achieves the desired therapeutic result in a subject. The mutual prodrug compound may be administered as a pharmaceutical composition, or in the absence of a carrier or diluent. Naturally, the dosages of the various mutual prodrugs will vary somewhat depending upon the components of the prodrugs, the rate of in vivo hydrolysis, etc. Those skilled in the art can determine the optimal dosing of the mutual prodrug compound based on clinical experience and the treatment indication.

Preferably, the amount of the mutual prodrug compounds administered to a subject is about 0.1 to about 100 mg/kg of body weight, more preferably, about 5 to about 40 mg/kg. Other preferred dosages include about 0.1 to about 10 mg/kg of body weight, about 1 to about 100 mg/kg of body weight, about 1 to about 60 mg/kg of body weight, about 1 to about 10 mg/kg of body weight, about 10 to about 100 mg/kg of body weight, about 10 to about 60 mg/kg of body weight, about 20 to about 60 mg/kg of body weight and about 30 to about 50 mg/kg of body weight.

The mutual prodrug compounds can also be converted into a pharmaceutically acceptable salt or pharmaceutically acceptable solvate or other physical forms (e.g., polymorphs) via known methods in the art field.

The subjects that may be treated using the compounds of the present invention include mammals, such as humans.

The present invention also includes the use of one or more of the mutual prodrug compound of the present invention as a medical treatment of a disease such as an autoimmune disease or cancer.

The present invention also includes a kit comprising one or more of the mutual prodrug compound of the present invention and instructions for its use.

The following Examples are intended to further illustrate the present invention without limiting its scope.

Example 1: Synthesis of 5-mono-n-butyl-1'-CN-Ara-C

-continued

12

Step 1: Preparation of (2R,3R,4S,5S)-2-((benzoyloxy)methyl)-5-cyanotetrahydrofuran-3,4-diyl Dibenzoate (2)

To a solution of β-D-ribofuranose 1-acetate 2,3,5-tribenzoate (25.0 g, 49.6 mmol) in dichloromethane (DCM, 62 mL) was added cyanotrimethylsilane (27.9 mL, 223 mmol). The reaction mixture was treated with $BF_3 \cdot OEt_2$ (6.7 mL, 54.5 mmol), stirred at 25° C. for 4.5 h, then poured slowly into an aqueous sodium bicarbonate and extracted with diethyl ether. The combined ether layers were washed with brine, dried over $MgSO_4$, filtered and evaporated. The residue was purified by silica gel column chromatography (Hexane:EtOAc=3:1) to give the compound 2 (16.0 g, 44%) as a yellow oil.

$^1$H NMR (400 MHz, $CDCl_3$) δ 8.14-8.12 (m, 2H), 7.98-7.91 (m, 4H), 7.61-7.54 (m, 3H), 7.48-7.36 (m, 6H), 6.01 (t, J=5.2 Hz, 1H), 5.86 (t, J=5.6 Hz, 1H), 4.98 (d, J=4.0 Hz, 1H), 4.75-4.70 (m, 2H), 4.63-4.58 (m, 1H).

Step 2: Preparation of (2S,3R,4R,5R)-5-((benzoyloxy)methyl)-2-bromo-2-cyanotetrahydrofuran-3,4-diyl Dibenzoate (3)

To a solution of the compound 2 (16.0 g, 33.9 mmol) in α,α,α-trifluorotoluene (340 mL) was added N-bromosuccinimide (NBS)(14.5 g, 81.5 mmol) at 25° C. The reaction mixture was irradiated by mercury lamp, stirred at 110° C. for 2 h, and quenched by aqueous $Na_2S_2O_3$. The organic layer was washed with an aqueous sodium bicarbonate, dried over $MgSO_4$, filtered and evaporated under reduced pressure. The residue was purified by silica gel column chromatography (Hexane:EtOAc=4:1) to give the compound 3 (20.0 g, 75%) as a colorless oil.

$^1$H NMR (400 MHz, $CDCl_3$) δ 8.10-7.98 (m, 5H), 7.89-7.87 (m, 1H), 7.63-7.32 (m, 9H), 6.34 (d, J=4.8 Hz, 0.5H), 6.22-6.15 (m, 0.5H), 5.86 (dd, J=6.8, 2.8 Hz, 0.5H), 5.80 (d, 0.1=6.8 Hz, 0.5H), 5.02-4.97 (m, 0.5H), 4.92 (q, J=2.8 Hz, 0.5H), 4.84-4.73 (m, 1.5H), 4.61 (dd, J=12.4, 4.4 Hz, 0.5H).

Step 3: Preparation of ((2R,3S,4R,5R)-3-(benzoyloxy)-5-cyano-5-(2,4-dioxo-3,4-dihydropyrimidin-1(2H)-yl)-4-hydroxytetrahydrofuran-2-yl)methyl Benzoate (4)

The reaction mixture of the compound 3 (18.0 g, 33.8 mmol) obtained in the step 2,2,4-bis((trimethylsilyl)oxy)pyrimidine (15.2 g, 59.2 mmol) and silver trifluoromethanesulfonate (AgOTf) (13.0 g, 50.9 mmol) in acetonitrile (MeCN)/1,2-dichloroethene (DCE) (163 mL/163 mL) was stirred at 100° C. for 5 h, cooled down to 25° C. and quenched with brine. The precipitates were filtered off and the filtrate was extracted with DCM. The organic layer was dried over $MgSO_4$, filtered and evaporated. The residue was purified by silica gel column chromatography (DCM:EtOAc=5:1) to give the compound 4 (14.5 g, 64%) as a yellow solid.

$^1$H NMR (400 MHz, $CDCl_3$) δ 8.47 (br s, 1H), 8.07-7.92 (m, 6H), 7.70 (d, J=8.4 Hz, 1H), 7.62-7.53 (m, 3H), 7.48-7.34 (m, 6H), 6.33 (d, J=5.6 Hz, 1H), 5.88 (t, J=5.6 Hz, 1H), 5.61 (d, J=8.4 Hz, 1H), 5.07-5.04 (m, 1H), 4.93 (dd, J=13.2, 2.8 Hz, 1H), 4.58 (dd, J=12.8, 3.2 Hz, 1H).

Step 4: Preparation of ((2R,3S,4R,5R)-3-(benzoyloxy)-5-cyano-5-(2,4-dioxo-3,4-dihydropyrimidin-1(2H)-yl)-4-hydroxytetrahydrofuran-2-yl)methyl Benzoate (5)

To a cooled (−60° C.) solution of the compound 4 (14.5 g, 24.9 mmol) in tetrahydrofuran (THF, 579 mL) was added potassium t-butoxide (10.1 g, 89.6 mmol). The reaction mixture was stirred at −60° C. for 0.5 h and quenched with trifluoroacetic acid (TFA) at same temperature. After warmed up to 25° C., the precipitates were filtered off and the filtrate was extracted with DCM. The combined organic layer was dried over $MgSO_4$, filtered and evaporated. The residue was purified by silica gel column chromatography (DCM:EtOAc=5:1) to give the compound 5 (9.2 g, 77%) as a white solid.

$^1$H NMR (400 MHz, $CDCl_3$) δ 9.12 (br s, 1H), 8.13 (d, J=7.2 Hz, 2H), 7.88 (d, J=7.6 Hz, 2H), 7.64 (d, J=8.4 Hz, 1H), 7.58 (q, J=7.6 Hz, 2H), 7.48-7.41 (m, 4H), 5.73-5.69 (m, 2H), 5.12 (br s, 1H), 5.02 (q, J=3.2 Hz, 1H), 4.96 (d, J=5.2 Hz, 1H), 4.92-4.88 (m, 1H), 4.52-4.48 (m, 1H).

Step 5: Preparation of ((2R,3R,4R,5R)-3-(benzoyloxy)-5-cyano-5-(2,4-dioxo-3,4-dihydropyrimidin-1(2H)-yl)-4-((methylsulfonyl)oxy)tetrahydrofuran-2-yl)methyl Benzoate (6)

To a cooled (0° C.) solution of the compound 5 (8.7 g, 18.2 mmol) in pyridine (260 mL) was added mesyl chloride (MsCl) (2.2 mL, 28.37 mmol). The reaction mixture was stirred at 25° C. for 6 h. After evaporated, the residue was diluted with EtOAc, washed with an aqueous sodium bicarbonate and brine. The organic layer was dried over $MgSO_4$, filtered and evaporated. The residue was purified by silica gel column chromatography (Hexane:EtOAc=1:1) to give the compound 6 (7.5 g, 78%) as a white solid.

$^1$H NMR (400 MHz, DMSO-d6) δ 11.88 (s, 1H), 8.04-7.98 (m, 4H), 7.78 (d, J=8.4 Hz, 1H), 7.68 (t, J=7.6 Hz, 2H), 7.54-7.47 (m, 4H), 5.91-5.85 (m, 2H), 5.50 (dd, J=8.4, 2.0 Hz, 1H), 5.02-4.98 (m, 1H), 4.72-4.59 (m, 2H), 3.49 (s. 3H).

Step 6: Preparation of ((2R,3R,3aS,9aR)-3-(benzoyloxy)-9a-cyano-6-oxo-2,3,3a,9a-tetrahydro-6H-furo[2',3':4,5]oxazolo[3,2-a]pyrimidin-2-yl)methyl Benzoate (7)

To a solution of the compound 6 (7.5 g, 13.5 mmol) and trimethylamine ($Et_3N$) (9.4 mL, 67.5 mmol) in MeCN (135 mL) was stirred at 70° C. for 1.5 h. After evaporated, the residue was diluted with DCM and washed with 1 N HCl and brine. The organic layer was dried over $MgSO_4$, filtered and evaporated to give the compound 7 (5.9 g, 95%) as a white solid.

$^1$H NMR (400 MHz, CDCl$_3$) δ 8.07 (d, J=8.8 Hz, 2H), 7.94 (d, J=8.4 Hz, 2H), 7.70-7.44 (m, 7H), 6.17 (d, J=7.6 Hz, 1H), 5.84 (dd, J=2.8, 1.2 Hz, 1H), 5.83 (s, 1H), 5.03-5.00 (m, 1H), 4.61-4.51 (m, 2H).

Step 7: Preparation of ((2R,3S,4S,5R)-3-(benzoyloxy)-5-cyano-5-(2,4-dioxo-3,4-dihydropyrimidin-1(2H)-yl)-4-hydroxytetrahydrofuran-2-yl)methyl Benzoate (8)

To a solution of the compound 7 (6.5 g, 14.2 mmol) and 1N HCl (141 mL) in dimethylformamide (DMF) (176 mL) was stirred at 40° C. for 5 h. After evaporated, the residue was diluted with DCM and washed with an aqueous sodium bicarbonate and brine. The organic layer was dried over MgSO$_4$, filtered and evaporated. The residue was purified by silica gel column chromatography (DCM:EtOAc=5:1) to give the compound 8 (6.4 g, 94%) as a white solid.

$^1$H NMR (400 MHz, DMSO-d$_6$) δ 11.73 (s, 1H), 8.09-8.03 (m, 4H), 7.73-7.65 (m, 3H), 7.59-7.51 (m, 4H), 7.18 (d, J=5.2 Hz, 1H), 5.67 (d, J=8.4 Hz, 1H), 5.44 (s, 1H), 5.01 (t, J=5.2 Hz, 1H), 4.87 (d, J=5.2 Hz, 1H), 4.56 (d, J=8.0 Hz, 2H).

Step 8: Preparation of (2R,3R,4S,5R)-4-acetoxy-2-((benzoyloxy)methyl)-5-cyano-5-(2,4-dioxo-3,4-dihydropyrimidin-1(2H)-yl)tetrahydrofuran-3-yl Benzoate (9)

The reaction mixture of the compound 8 (6.4 g, 13.4 mmol), 4-dimethylaminopyridine (DMAP) (164 mg, 0.8 mmol) and acetic anhydride (Ac$_2$O) (6.4 mL) in pyridine (176 mL) was stirred at 25° C. for 5 h. After evaporated, the residue was diluted with EtOAc and washed with an aqueous sodium bicarbonate and brine. The organic layer was dried over MgSO$_4$, filtered and evaporated. The residue was purified by silica gel column chromatography (Hexane:EtOAc=1:1) to give the compound 9 (6.7 g, 94%) as a white solid.

$^1$H NMR (400 MHz, CDCl$_3$) δ 9.43 (br s, 1H), 8.13 (d, J=7.2 Hz, 2H), 8.05 (d, J=7.2 Hz, 2H), 7.71 (d, J=8.4 Hz, 1H), 7.65-7.59 (m, 2H), 7.51-7.45 (m, 4H), 6.16 (s, 1H), 5.82 (d, J=8.4 Hz, 1H), 5.49 (d, J=2.8 Hz, 1H), 4.99 (dd, J=12.4, 2.8 Hz, 1H), 4.87-4.84 (m, 1H), 4.76 (dd, J=12.4, 4.8 Hz, 1H).

Step 9: Preparation of (2R,3S,4S,5R)-5-(4-amino-2-oxopyrimidin-1(2H)-yl)-2-((benzoyloxy)methyl)-5-cyano-4-hydroxytetrahydrofuran-3-yl Benzoate 10)

To a solution of the compound 9 (2.8 g, 5.5 mmol), DMAP (1.4 g, 12.0 mmol), Et$_3$N (1.7 mL, 12.0 mmol) and 2,4,6-triisopropylbenzenesulfonyl chloride (3.6 g, 12.0 mmol) in MeCN (128 mL) was stirred at 25° C. for 2 h. After cooled to 0° C., the reaction mixture was treated with aqueous NH$_4$OH (35 mL) and stirred at 25° C. for 2 h. After evaporated, the residue was diluted with EtOAc and washed with an aqueous sodium bicarbonate and brine. The organic layer was dried over MgSO$_4$, filtered and evaporated. The residue was purified by silica gel column chromatography (DCM:MeOH=13:1) to give the compound 10 (1.5 g, 57%) as a white solid.

$^1$H NMR (400 MHz, methanol-d$_4$) δ 8.17-8.10 (m, 4H), 7.81 (d, J=8.0 Hz, 1H), 7.68-7.60 (m, 2H), 7.54-7.47 (m, 4H), 5.9 (d, J=7.6 Hz, 1H), 5.48 (s, 1H), 5.12 (s, 1H), 4.94-4.91 (m, 1H), 4.83-4.70 (m, 2H).

Step 10: Preparation of (2R,3S,4S,5R)-2-(4-amino-2-oxopyrimidin-1(2H)-yl)-3,4-dihydroxy-5-hydroxymethyl)tetrahydrofuran-2-carbonitrile (11, Formula (II))

The reaction mixture of the compound 10 (500 mg, 1.1 mmol) in 7 N NH$_3$ in MeOH (10.4 mL) was stirred at 25° C. for 4 h and directly purified by silica gel column chromatography (DCM:MeOH=4:1) to give the compound 11 (240 mg, 82%) as a white solid.

$^1$H NMR (400 MHz, D$_2$O) δ 7.7 (d, J=7.6 Hz, 1H), 5.89 (d, J=7.6 Hz, 1H), 4.71 (s, 1H), 4.32-4.29 (m, 1H), 4.06-4.04 (m, 1H), 3.75-3.61 (m, 2H).

Step 11: Preparation of ((2R,3S,4S,5R)-5-(4-amino-2-oxopyrimidin-1(2H)-yl)-5-cyano-3,4-dihydroxytetrahydrofuran-2-yl)methyl Butyrate (12)

To a solution of the compound 11 (700 mg, 2.6 mmol) in dimethylacetamide (DMA, 9.6 mL) was added 1 M HCl in ether (3.1 mL). The reaction mixture was stirred at 25° C. for 1 h and then treated with butyryl chloride (330 L, 3.1 mmol) in dimethylacetamide (5.1 mL). The reaction mixture was stirred at 25° C. for 1 h and evaporated under reduced pressure. The residue was diluted with EtOAc and washed with an aqueous sodium bicarbonate and brine. The organic layer was dried over MgSO$_4$, filtered and evaporated. The residue was purified by silica gel column chromatography (DCM:MeOH=9:1) to give the compound 12 (500 mg, 70%) as a white solid.

$^1$H NMR (400 MHz, methanol-d$_4$) δ 7.72 (d, J=7.6 Hz, 1H), 5.89 (d, J=7.6 Hz, 1H), 4.79 (s, 1H), 4.48-4.44 (m, 1H), 4.40-4.27 (m, 2H), 4.1 (s, 1H), 2.35 (t, J=7.2 Hz, 2H), 1.68-1.62 (m, 2H), 0.951 (t, J=7.6 Hz, 3H).

MS (EI) for C$_{14}$H$_{18}$N$_4$O$_6$. found 339.1 (MH+).

Example 2: Synthesis of 5-Mono-N-Butyl-Zebularine (21)

16

17

18

19

20

21

Step 1: Preparation of 2-(2-(trimethylsilyl)ethoxy)pyrimidine (14)

To a cooled (0° C.) solution of NaH (7.9 g, 331.8 mmol) in THF (190 mL) was added 2-(trimethylsilyl)ethanol (9.8 g, 82.9 mmol). The reaction mixture was stirred at 0° C. for 1 h, treated with the compound 13 (9.5 g, 82.9 mmol) and stirred at 25° C. for additional 24 h. The reaction mixture was quenched with water and extracted with EtOAc. The combined organic layer was dried over MgSO$_4$, filtered and concentrated under reduced pressure. The residue was purified by silica gel column chromatography (Hexane:EtOAc=2:1) to give the compound 14 (17.0 g, 99%) as a yellow oil.

$^1$HNMR (400 MHz, CDCl$_3$) δ 8.49 (d, J=5.2 Hz, 1H), 6.89 (t, J=4.6 Hz, 1H), 4.46-4.42 (m, 2H), 1.21-1.17 (m, 2H), 0.08 (s, 9H).

Step 2: Preparation of (2R,3R,4R,5R)-2-((benzoyloxy)methyl)-5-(2-oxopyrimidin-1(2H)-yl)tetrahydrofuran-3,4-diyl Dibenzoate (15)

To a solution of the compound 14 (5.9 g, 29.8 mmol) and β-D-ribofuranose 1-acetate 2,3,5-tribenzoate (15 g, 29.9 mmol) in anhydrous MeCN (370 mL) was added TMS-triflate (5.9 g, 26.8 mmol) at 25° C. under N$_2$ gas atmosphere. After stirred at 25° C. for 1.5 h, the reaction mixture was evaporated under reduced pressure. The residue was immediately dissolved in DCM and washed with an aqueous sodium bicarbonate, brine and water. The organic layer was dried over. MgSO$_4$, filtered and concentrated under reduced pressure. The residue was purified by silica gel column chromatography (Hexane:EtOAc=1:4) to give the compound 15 (7.3 g, 45%) as a white solid.

$^1$HNMR (400 MHz, CDCl$_3$) δ 8.61 (s, 1H), 8.09-8.07 (m, 3H), 7.98-7.91 (m, 4H), 7.59-7.46 (m, 5H), 7.40-7.36 (m, 4H), 6.41 (d, J=3.6 Hz, 1H), 6.26 (dd, J=6.8, 4.4 Hz, 1H), 5.90 (d, J=5.6 Hz, 1H), 5.76 (dd, J=5.2, 4.0 Hz, 1H), 4.90-4.82 (m, 2H), 4.71 (dd, J=12.4, 4.0 Hz, 1H).

Step 3: Preparation of 1-((2R,3R,4S,5R)-3,4-dihydroxy-5-(hydroxymethyl)tetrahydrofuran-2-yl)pyrimidin-2(1H)-one (16)

To a cooled (0° C.) solution of the compound 15 (9.5 g, 17.6 mmol) in MeOH (100 mL) was added 7N NH$_3$ in MeOH (245 mL). The reaction mixture was stirred at 25° C. for 24 h and evaporated under reduced pressure. The residue was diluted with water and extracted with chloroform. The organic layer was dried over MgSO$_4$, filtered and concentrated under reduced pressure. The residue was purified by silica gel column chromatography (DCM:MeOH=10:1) to give the compound 16 (3.8 g, 94%) as a white solid.

$^1$HNMR (400 MHz, methanol-d$_4$) δ 8.79 (dd, J=6.8, 2.8 Hz, 1H), 8.57 (dd, J=4, 2.8 Hz, 1H), 6.58 (dd, J=6.8, 4.4 Hz, 1H), 5.86 (s, 1H), 4.15-4.10 (m, 3H), 3.98 (dd, J=12.4, 2.0 Hz, 1H), 3.79 (dd, J=12.8, 2.0 Hz, 1H).

Step 4: Preparation of 1-((2R,3R,4S,5R)-3,4-dihydroxy-5-(((3-methoxyphenyl)(4-methoxyphenyl)(phenyl)methoxy)methyl)tetrahydrofuran-2-yl)pyrimidin-2(1H)-one (17)

To a cooled (0° C.) solution of the compound 16 (3.0 g, 13.2 mmol) in pyridine (33 mL) was added 4,4'-dimethoxytriphenylmethyl chloride (DMTCl) (5.6 g, 16.5 mmol) and the reaction mixture was stirred at 25° C. for 50 min.

After evaporated under reduced pressure, the residue was purified by silica gel column chromatography (DCM:MeOH=20:1) to give the compound 17 (4.4 g, 63%) as a white solid.

$^1$HNMR (400 MHz, CDCl$_3$) δ 8.63 (dd, J=4.4, 3.2 Hz, 1H), 8.40 (dd, J=5.6, 2.4 Hz, 1H), 7.63-7.16 (m, 9H), 6.84-6.81 (m, 4H), 6.14 (dd, J=6.8, 4.0 Hz, 1H), 5.87 (d, J=3.2 Hz, 1H), 4.43-4.39 (m, 3H), 3.80 (s, 6H), 3.51-3.41 (m, 2H).

Step 5: Preparation of 1-((2R,3R,4R,5R)-5-((bis(4-methoxyphenyl) (phenyl)methoxy)methyl)-3,4-bis((tert-butyldimethylsilyl)oxy)tetrahydrofuran-2-yl)pyrimidin-2(1H)-one (18)

To a solution of the compound 17 (5.6 g, 10.6 mmol) in anhydrous DMF (45 mL) were added imidazole (5.1 g, 74.2 mmol) and tert-butylchlorodimethylsilane (TBSCl) (8 g, 52.8 mmol). The reaction mixture was stirred at 25° C. for 15 h, quenched with water and extracted with EtOAc. The combined organic layers were washed with an aqueous sodium bicarbonate, dried over MgSO$_4$, filtered and concentrated under reduced pressure. The residue was purified by silica gel column chromatography (DCM:MeOH=97:3) to give the compound 18 (6.3 g, 85%) as a pale yellow solid.

$^1$HNMR (400 MHz, CDCl$_3$) δ 8.84 (dd, J=6.8, 2.8 Hz, 1H), 8.48 (dd, J 3.6, 2.4 Hz, 1H), 7.35-7.16 (m, 9H), 6.85-6.82 (m, 4H), 5.79 (dd, J=6.4, 4.0 Hz, 1H), 5.75 (s, 1H), 4.28-4.24 (m, 1H), 4.19-4.13 (m, 2H), 3.84 (dd, J=10.8, 2.0 Hz, 1H), 3.80 (s, 6H), 3.34 (dd, J=11.2, 2.0 Hz, 1H), 0.90 (s, 9H), 0.88 (s, 9H), 0.31 (s, 3H), 0.14 (s, 3H), 0.05 (s, 3H), 0.01 (s, 3H).

Step 6: Preparation of 1-((2R,3R,4R,5R)-3,4-bis((tert-butyldimethylsilyl)oxy)-5-(hydroxymethyl)tetrahydrofuran-2-yl)pyrimidin-2(1H)-one (19)

To the compound 18 (6.3 g, 8.5 mmol) was added solution of 3% TFA (8.5 mL) in DCM (284 mL) at 25° C. The reaction mixture was stirred at same temperature for 5 min, quenched with MeOH and concentrated under reduced pressure. Immediately, the residue was purified by silica gel column chromatography (Hexane:EtOAc=1:1 to neat EtOAc) to give the compound 19 (3.9 g, 98%) as a white solid.

$^1$HNMR (400 MHz, CDCl$_3$) δ 8.67 (dd, J=4.4, 2.8 Hz, 1H), 8.41 (dd, J 6.8, 2.8 Hz, 1H), 6.41 (dd, J=6.4, 4.0 Hz, 1H), 5.52 (d, J=3.2 Hz, 1H), 4.54 (t, J=3.4 Hz, 1H), 4.20-4.07 (m, 3H), 3.78 (dd, J=12.4, 1.6 Hz, 1H), 0.88 (s, 18H), 0.11 (s, 3H), 0.09 (s, 3H), 0.06 (s, 6H).

Step 7: Preparation of ((2R,3R,4R,5R)-3,4-bis((tert-butyldimethylsilyl)oxy)-5-(2-oxopyrimidin-1(2H)-yl)tetrahydrofuran-2-yl)methyl Butyrate (20)

To a stirred solution of the compound 19 (3.8 g, 8.3 mmol), pyridine (14 mL) and butyric anhydride (2.7 mL, 16.6 mmol) was added DMAP (203 mg, 1.6 mmol). The reaction mixture was stirred at 25° C. for 15 h and concentrated under reduced pressure. The residue was purified by silica gel column chromatography (Hexane:EtOAc=4:1 to Hexane:EtOAc=1:1) to give the compound 20 (2.7 g, 62%) as a colorless oil.

$^1$HNMR (400 MHz, CDCl$_3$) δ 8.62 (dd, J=4.0, 2.8 Hz, 1H), 8.33 (dd, J=6.8, 2.8 Hz, 1H), 6.33 (dd, J=6.8, 4.0 Hz, 1H), 5.64 (s, 1H), 4.46-4.33 (m, 3H), 4.28 (d, J=4.0 Hz, 1H), 3.85 (dd, J=8.4, 3.6 Hz, 1H), 2.35-2.31 (m, 2H), 1.72-1.63 (m, 2H), 1.01-0.97 (m, 3H), 0.94 (s, 9H), 0.86 (s, 9H), 0.32 (s, 3H), 0.17 (s, 3H), 0.01 (s, 3H), 0.01 (s, 3H).

Step 8: Preparation of ((2R,3S,4R,5R)-3,4-dihydroxy-5-(2-oxopyrimidin-1(2H)-yl)tetrahydrofuran-2-yl)methyl Butyrate (21)

To the cooled (0° C.) solution of the compound 20 (2.7 g, 5.1 mmol) in THF (51 mL) was added 1M tetrabutylammonium fluoride (TBAF) (10 mL) dropwise. The reaction mixture was stirred at −20° C. for 10 min and then immediately loaded to the silica gel column without concentration (neat DCM to DCM:MeOH=20:1) to give the compound 21 (1.0 g, 67%) as a white solid.

$^1$HNMR (400 MHz, CDCl$_3$) δ 8.66 (dd, J=4.0, 2.8 Hz, 1H), 8.19 (dd, J=6.8, 2.8 Hz, 1H), 6.48 (dd, J=6.8, 4.0 Hz, 1H), 5.84 (d, J=4.0 Hz, 1H), 4.53-4.43 (m, 1H), 4.41 (dd, J=12.4, 2.8 Hz, 1H), 4.33 (dd, J=12.4, 4.0 Hz, 1H), 4.26-4.17 (m, 2H), 2.25-2.19 (m, 2H), 1.63-1.57 (m, 2H), 0.97-0.90 (m, 3H).

MS (EI) for C$_{13}$H$_{18}$N$_2$O$_6$. found 299.1 (MH$^+$).

Example 3: Synthesis of 2',3',5'-Tri-N-Butyl-Zebularine (22)

Preparation of (2R,3R,4R,5R)-2-((butyryloxy)methyl)-5-(2-oxopyrimidin-1(2H)-yl)tetrahydrofuran-3,4-diyl Dibutyrate (22)

To a solution of the compound 16 (1.0 g, 4.4 mmol) in pyridine (12.5 mL) was added butyric anhydride (12.5 mL) and DMAP (37.5 mg, 0.31 mmol) at 25° C. The reaction mixture was stirred at same temperature for 4 h and evaporated under reduced pressure. The residue was dissolve in DCM and washed with an aqueous sodium bicarbonate. The organic layer was dried over MgSO$_4$, filtered and concentrated under reduced pressure. The residue was purified by silica gel column chromatography (Hexane:EtOAc=1:1) to give the compound 22 (900 mg, 47%) as a pale yellow oil.

$^1$HNMR (400 MHz, CDCl$_3$) δ 8.62 (dd, J=4.0, 2.8 Hz, 1H), 8.06 (dd, J=6.8, 2.8 Hz, 1H), 6.39 (dd, J=6.8, 4.4 Hz, 1H), 6.10 (d, J=4.0 Hz, 1H), 5.42 (dd, J=5.6, 4.0 Hz, 1H), 5.24 (t, J=5.6 Hz, 1H), 4.43-4.37 (m, 3H), 2.37-2.30 (m, 6H), 1.69-1.59 (m, 6H), 0.95-0.91 (m, 9H).
MS (EI) for C$_{21}$H$_{30}$N$_2$O$_8$. found 439.2 (MH$^+$).

Example 4: Synthesis of 2',3',5'-tri-isobutyl-zebularine (23)

Preparation of (2R,3R,4R,5R)-2-((isobutyryloxy)methyl)-5-(2-oxopyrimidin-1(2H)-yl)tetrahydrofuran-3,4-diyl bis(2-methylpropanoate) (23)

To a solution of the compound 16 (1.0 g, 4.4 mmol) in pyridine (12.5 mL) was added iso-butyric anhydride (12.5 mL) and DMAP (37.5 mg, 0.31 mmol) at 25° C. The reaction mixture was stirred at same temperature for 15 h and evaporated under reduced pressure. The residue was dissolve in DCM and washed with an aqueous sodium bicarbonate. The organic layer was dried over MgSO$_4$, filtered and concentrated under reduced pressure. The residue was purified by silica gel column chromatography (Hexane:EtOAc=1:1) to give the compound 23 (1.0 g, 52%) as a white solid.
$^1$HNMR (400 MHz, DMSO-d$_6$) δ 8.59 (t, J=3.4 Hz, 1H), 8.17 (dd, J=6.4, 2.8 Hz, 1H), 6.52 (dd, J=6.8, 4.0 Hz, 1H), 5.88 (d, J=3.2 Hz, 1H), 5.48 (dd, J=6.0, 3.6 Hz, 1H), 5.36 (t, J=6.2 Hz, 1H), 4.38-4.24 (m, 3H), 2.58-2.51 (m, 3H), 1.06 (dd, J=6.8, 3.2 Hz, 18H).
MS (EI) for C$_{21}$H$_{30}$N$_2$O$_8$. found 439.1 (MH$^+$).

Test Example 1: Cytidine Deaminase (CDA) Assay

Activities of human cytidine deaminase on cytidine, Ara-C and Compound 11 were compared.
His$_6$-tagged, *E. coli*-purified recombinant human cytidine deaminase (CDA) was incubated with 0.01 mM of each of the cytidine, Ara-C and Compound 11, respectively, in a 1 mL reaction, containing 20 mM Tris-HCl (pH 8.0), 1 mM DTT, 2 mM EDTA, 100 mM NaCl and 40% glycerol at 25° C. Changes in observance at OD$_{282}$ were recorded at every 10 seconds for 3 minutes using the continuous spectrophotometric method (A. Amici, et al., Br. J. Haematol., 1989; 73(3): 392-395).

TABLE 1

| Compound | Relative rxn velocity |
|---|---|
| cytidine | 1 |
| Ara-C | 0.4 |
| 11 | <0.01 |

Figure 1:
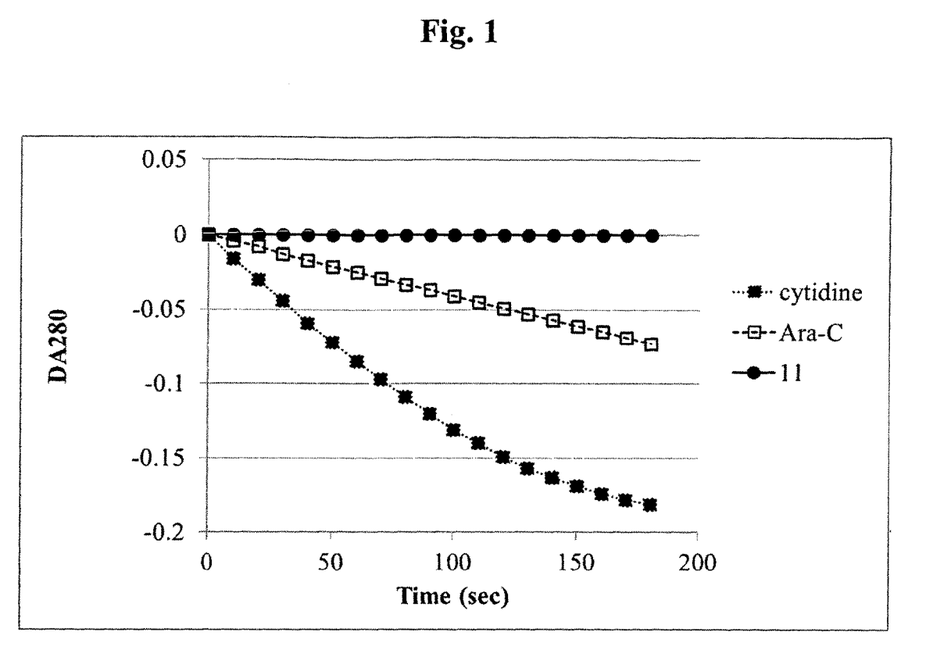
FIG. 1: Relative susceptibility of cytidine, Ara-C and Compound 11 to cytidine deaminase.

As shown in Table 1, and FIG. 1, Compound 11 is resistant to deamination by CDA.

Test Example 2: Anti-Proliferative Activity Test

Anti-proliferative activities in IC$_{50}$ (uM) of Ara-C (cytarabine), Compound 11 (Comparative example) and Compound 12 (Example 1) against hematological cancer (MOLT-4, MV-4-11 and HL-60), liver cancer (Hep G2) and colon cancer (HCT 116) cell lines (Corning #3603) were compared.
CellTiter-Glo® Luminescent Cell Viability Assay (Promega #G7572) was used to measure the 50% inhibition concentration (IC$_{50}$) of the Ara-C and Compounds 11 and 12 against MOLT-4 (human acute lymphoblastic leukemia), MV-4-11 (human biphenotypic B myelomonocytic leukemia), HL-60 (human acute promyelocytic leukemia), Hep G2 (human hepatocellular carcinoma) and HCT 116 (human colorectal carcinoma) cell lines. Six hundred cells in 90 media were plated per well in duplicates in a 96-well plate. Cells were incubated in a humidified incubator at 37° C. with 5% CO$_2$ during the assay. DMSO was added to the test compounds with the final DMSO concentration being 0.1% [v/v] of the culture. 100 µl of CellTiter-Glo® was added to the equal volume of cultured cells to read luminescence in EnVision Multi Label Reader. The results are shown in Table 2 below.

TABLE 2

| | | IC$_{50}$ (uM) | | |
|---|---|---|---|---|
| Cancer type | Cell line | Ara-C | Compound 11 | Compound 12 |
| hematological | MOLT-4 | 0.02 | 1.06 | 1.14 |
| hematological | MV-4-11 | 3.1 | 5.0 | 0.13 |
| hematological | HL-60 | 0.63 | 2.41 | 5.06 |
| liver cancer | Hep G2 | 1.91 | 6.0 | 0.56 |
| colon cancer | HCT 116 | 0.29 | 0.96 | 0.22 |

As shown in Table 2, Compound 12 prepared in Example 1 exhibits the proliferative activities on hematological cancer, liver cancer and colon cancer cells.

Test Example 3: Animal Pharmacokinetics of Compound 12

Pharmacokinetics of Compound 12 prepared in Example 1 were evaluated in ICR mice and SD rats following intravenous (IV) administration at 10 mg/kg and peroral (PO) administration at 10 mg/kg dose level, respectively.
For serum compound analysis, blood samples were collected by cardiac puncture over 24 hr time course. 20 µl of spiked plasma was added into 96 well plate, adding ten volumes of internal standard (IS) in acetonitrile (ACN) to precipitate proteins, mixed fully, centrifuged for 10 min at 4,000 rpm. 150 µl of supernatant was transferred to another pre-labeled 96 well plate, mixed with 150 µl of water, then injected 5 µl or 10 µl into the liquid chromatography-mass spectrometry (LC-MS) system under the following conditions:

Column: API-4000+Waters UPLC (TCLM08);
Mobile phase: water:MeOH=100:0, 30:70, 5:95 and 100:0 (v/v %);
Flow rate: 0.45 mL/min.
Lower limit of quantification (LLOQ) was at 1 ng/mL. Pharmacokinetic parameters of half-life ($T_{1/2}$), clearance (CL), maximum plasma concentration ($C_{max}$), time when the maximal serum concentration of compound is achieved ($T_{max}$) and bioavailability (F %), exposure (AUC) and volume of distribution ($V_{ss}$) of the compound were calculated using Phoenix WinNonlin 6.3 (non-compartmental model). The results are shown in Table 3, and FIGS. 2 and 3.

TABLE 3

| Animal | route | mpk (mg) | $T_{1/2}$ (hr) | CL (mL/min/kg) | F % |
|---|---|---|---|---|---|
| mouse | IV | 10 | 3.1 | 21.6 | — |
|  | PO | 10 | 4.6 | — | 62 |
| rat | IV | 10 | 3.1 | 11.4 | — |
|  | PO | 10 | 2.5 | — | 48.8 |

Figure 2:
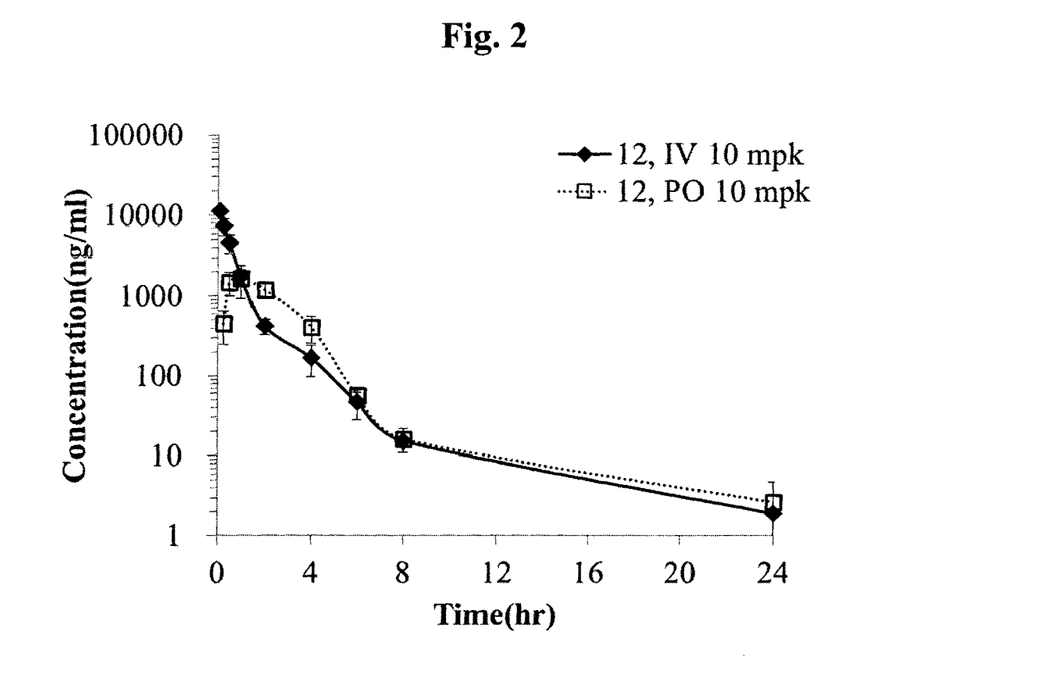
FIG. 2: Mouse pharmacokinetics of the Compound 12 of Example 1 through IV and PO administration route.
Figure 3:
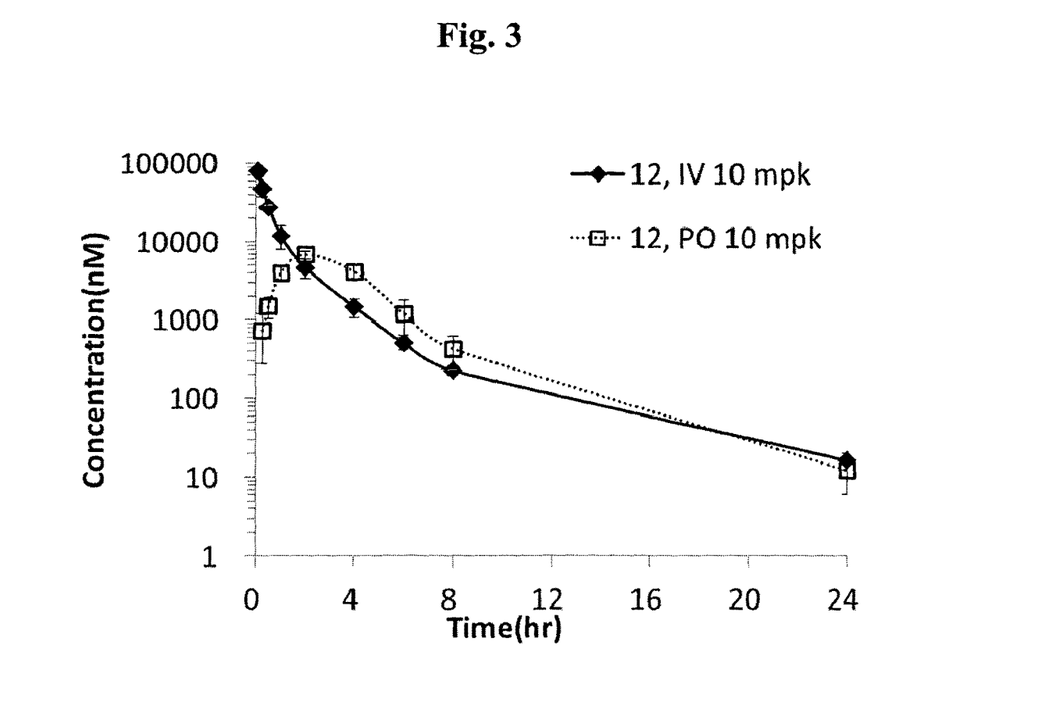
FIG. 3: Rat pharmacokinetics of the Compound 12 of Example 1 through IV and PO administration route.

As shown in Table 3 and FIGS. 2 and 3, Compound 12 exhibits good mouse and rat PK, both in IV and PO routes.

Test Example 4: Efficacy of PO-Administered Compound 12 in HL-60 Human Leukemia Xenograft Tumor growth inhibition (TGI) activities of IP-administered Ara-C, and PO-administered Compound 12 were compared in HL-60 human leukemia xenografts.

Tumor growth inhibitions were observed in in vivo subcutaneous mouse xenograft model (HL-60 cell line, Corning #3603). NOD/SCID female mice of 6-8 weeks age and weighing approximately 18 to 22 g, were used for tumor inoculation. Each mouse was inoculated subcutaneously at the right flank with HL-60 cancer cells ($1\times10^7$ cells) in mixture of 100 μl of PBS and 100 μl of Matrigel™ for tumor development. Eight mice were used for each group (n=8/group). The amounts of treated compounds are represented in milligram (mg) of compound per kilogram (kg) of animal body weight (mg/kg, mpk). Administration route of the test compound was either intraperitoneal (IP) injection or peros (PO, oral) injection. Three groups, i.e., vehicle group (Control group), Ara-C group (treatment at 40 mpk of cytarabine through IP injection; Comparative group) and Compound 12 group (treatment at 60 mpk of Compound 12 through PO injection) of mice were used. The overall administration schedule was 2 cycles of treatment for 5 days (5 d ON), followed by 2 days of non-treatment (2 d OFF). Tumor sizes were measured using a caliper, once every 4 days, and the tumor volume was expressed in mm³ using Equation 1:

$$V=0.5a\times b^2 \quad \text{[Equation 1]}$$

Wherein, a and b are the long and short diameters of the tumor, respectively.

Figure 4A:
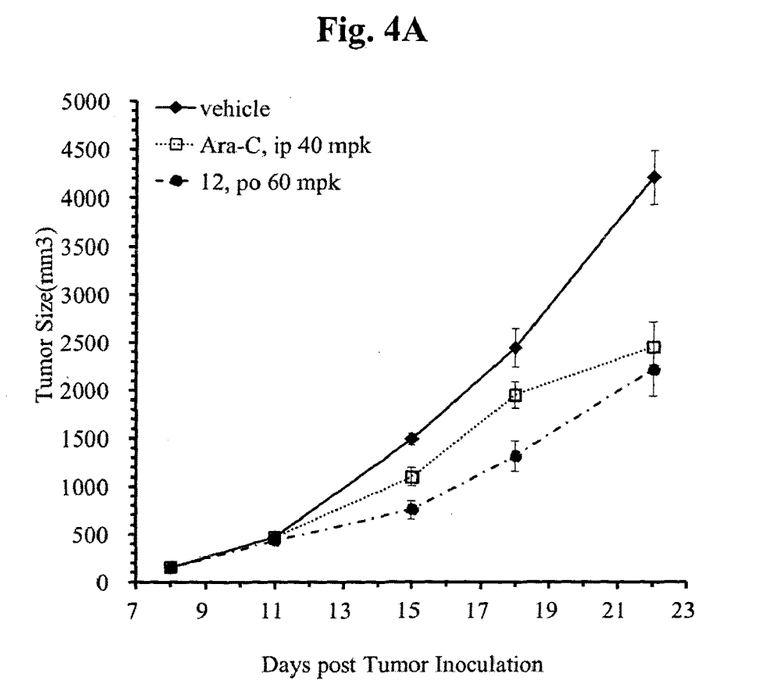
FIGS. 4A and 4B: The tumor volume and body weight of PO-administered Compound 12 of Example 1 in HL-60 human leukemia xenograft.
Figure 4B:
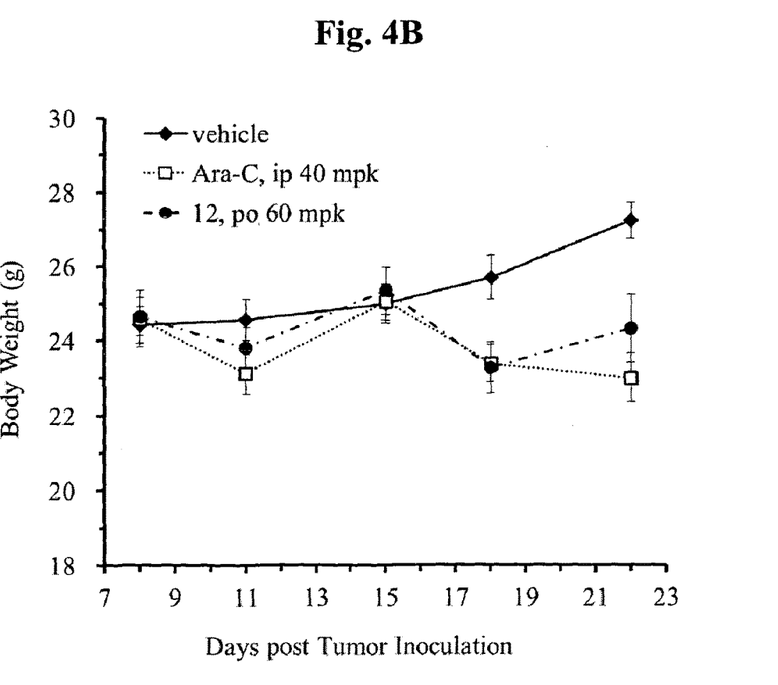

The tumor volume (mm³) and body weight (g) results of the three groups are shown in FIGS. 4A and 4B, respectively. Also, tumor growth inhibition (% TGI) and body weight change (% BW change) compared to that of Ara-C were shown in Table 4.

TABLE 4

| sample | route | administration schedule | % TGI | % BW change |
|---|---|---|---|---|
| Vehicle | IP | 5 d ON/2 d Off × 2 | 0 | +11.5 |
| Ara-C | 40 mpk, IP | 5 d ON/2 d Off × 2 | 46 | −6.2 |
| Compound 12 | 60 mpk, PO | 5 d ON/2 d Off × 2 | 50 | −0.9 |

As shown in Table 4, and FIGS. 4A and 4B, oral dosing of Compound 12 shows a comparable potency to IP dosing of Ara-C, with similar body weight changes.

Test Example 5: Tumor Growth Inhibition Efficacy of Compound 12

Tumor growth inhibition activities of IP-administered Ara-C and Compound 12 were compared in HL-60 human leukemia xenograft.

Tumor growth inhibitions were observed in in vivo subcutaneous mouse xenograft model (HL-60 cell line, Corning #3603). NOD/SCID female mice of 6-8 weeks age and weighing approximately 18 to 22 g, were used for tumor inoculation. Each mouse was inoculated subcutaneously at the right flank with HL-60 tumor cells ($1\times10^7$ cells) in mixture of 100 μl of PBS and 100 of μl Matrigel™ for tumor development. Eight mice were used for each group (n=8/group). The amounts of treated compounds are represented in milligram (mg) of compound per kilogram (kg) of animal body weight (mg/kg, mpk). Administration route of all test compounds was through IP injection. Five groups, i.e., vehicle group (Control group), Ara-C group (treatment at 60 mpk of cytarabine; Comparative group) and Compound 12 group (treatment at a various amounts of 20, 40 and 60 mpk of Compound 12), of mice were used. The overall administration schedule was 2 cycles of compound treatment for 5 days, followed by 2 days of non-treatment. Tumor sizes were measured using a caliper, once every 4 days, and the tumor volume was expressed in mm³ using Equation 1.

Figure 5A:
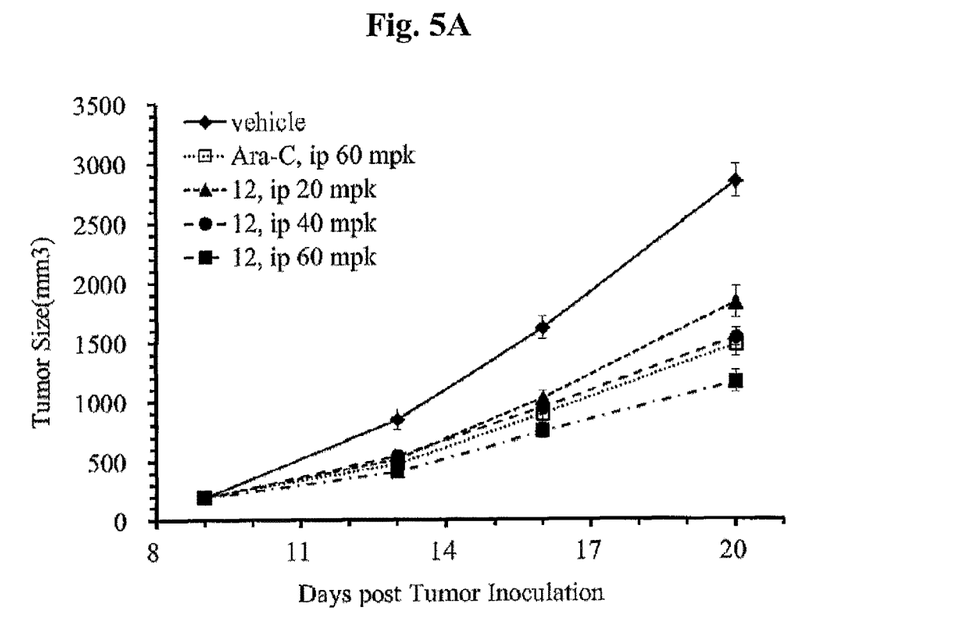
FIGS. 5A and 5B: The tumor volume and body weight change of IP-administered Compound 12 of Example 1 at various dose in HL-60 human leukemia xenograft.
Figure 5B:
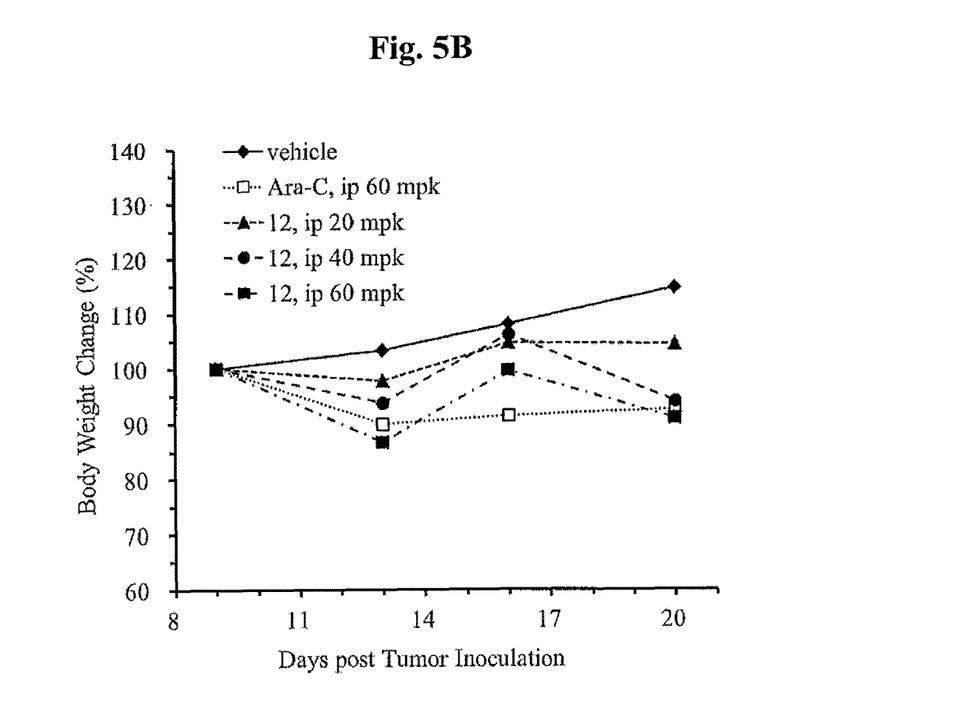

The tumor volume (mm³) and body weight (g) results of five groups are shown in FIGS. 5A and 5B, respectively. Also, tumor growth inhibition (% TGI) compared to that of Ara-C were shown in Table 5.

TABLE 5

|  | vehicle | Compound 12 | Compound 12 | Compound 12 | Ara-C |
|---|---|---|---|---|---|
| dose | — | 20 mpk | 40 mpk | 60 mpk | 60 mpk |
| TGI (%) | — | 36 | 46 | 59 | 60 |

As shown in Table 5, and FIGS. 5A and 5B, in IP dosing, Compound 12 at 40 mpk, at a half dose of (0.11 umole/kg) Ara-C at 60 mpk, exhibited a comparable TGI (%) to Ara-C at 60 mpk (0.25 umole/kg), with comparable body weight change.

Test Example 6: Pharmacokinetics of Compounds 16, 22 and 23

Pharmacokinetics of Compound 16 (Comparative example) prepared in step 3 of Example 2, and mutual prodrugs of Compounds 22 and 23 prepared in Example 3 and 4, respectively, were evaluated in SCID/mice following oral (PO) and intravenous (IV) administration according to the route/dose as shown in Table 4.

Blood samples were collected over 24 hrs, and plasma samples were prepared. Plasma concentrations of the test compounds were analyzed by LC/MS/MS. The maximum plasma concentration ($C_{max}$), exposure (AUC), bioavailability (F %), half-life ($T_{1/2}$), clearance (CL), volume of distribution ($V_{ss}$), time when the maximal serum concentration of compound is achieved ($T_{max}$) and mean residence time (MRT) were calculated as were in Test Example 3. The results are shown in Table 6.

TABLE 6

| Compounds | Route/dose (mpk) | $C_{max}$ (uM) | AUC (ug*hr · ml) | % F | $T_{1/2}$ (hr) | CL (ml/min/kg) | $V_{ss}$ (L/kg) | $T_{max}$ | MRT |
|---|---|---|---|---|---|---|---|---|---|
| 16 | IV/100 | — | 54.6 | — | 2.03 | 30.22 | 0.91 | — | — |
|    | PO/500 | 22.3 | 20.9 | 8.4 | 2.44 | — | — | — | — |
| 22 | PO/75 | 0.88 | 0.5 | 2.4 | 1.3 | — | — | 0.3 | 1.8 |
|    | PO/150 | 4.4 | 1.1 | 2.7 | 1.6 | — | — | 0.5 | 1.2 |
| 23 | PO/75 | 5.3 | 1.8 | 8.8 | 8.8 | — | — | 0.3 | 2.8 |
|    | PO/150 | 30.7 | 6.5 | 16 | 4.9 | — | — | 0.5 | 1.3 |

Test Example 7: Tumor Growth Inhibition Efficacy of Compounds 22 and 23

Tumor growth inhibition activities of Compounds 22 and 23 were compared in MOLT-4 xenograft.

Xenograft models were developed as were in Test Example 3, except for using MOLT-4 cell line (Corning #3603) instead of HL-60 cell line. Administration route of the test compound was either BID injection or QD injection. Three groups, i.e., vehicle group (Control group), Compound 22 group (treatment at 150 mpk of the compound 22 through BID or QD injection) and Compound 23 group (treatment at 150 mpk of the compound 23 through BID or QD injection) of mice were used. The overall administration schedule was 2 cycles of sample treatment for 5 days (5 d ON), followed by 2 days of non-treatment (2 d OFF). Tumor sizes were measured as were in Test Example 4. The results are shown in FIG. 6.

Figure 6:
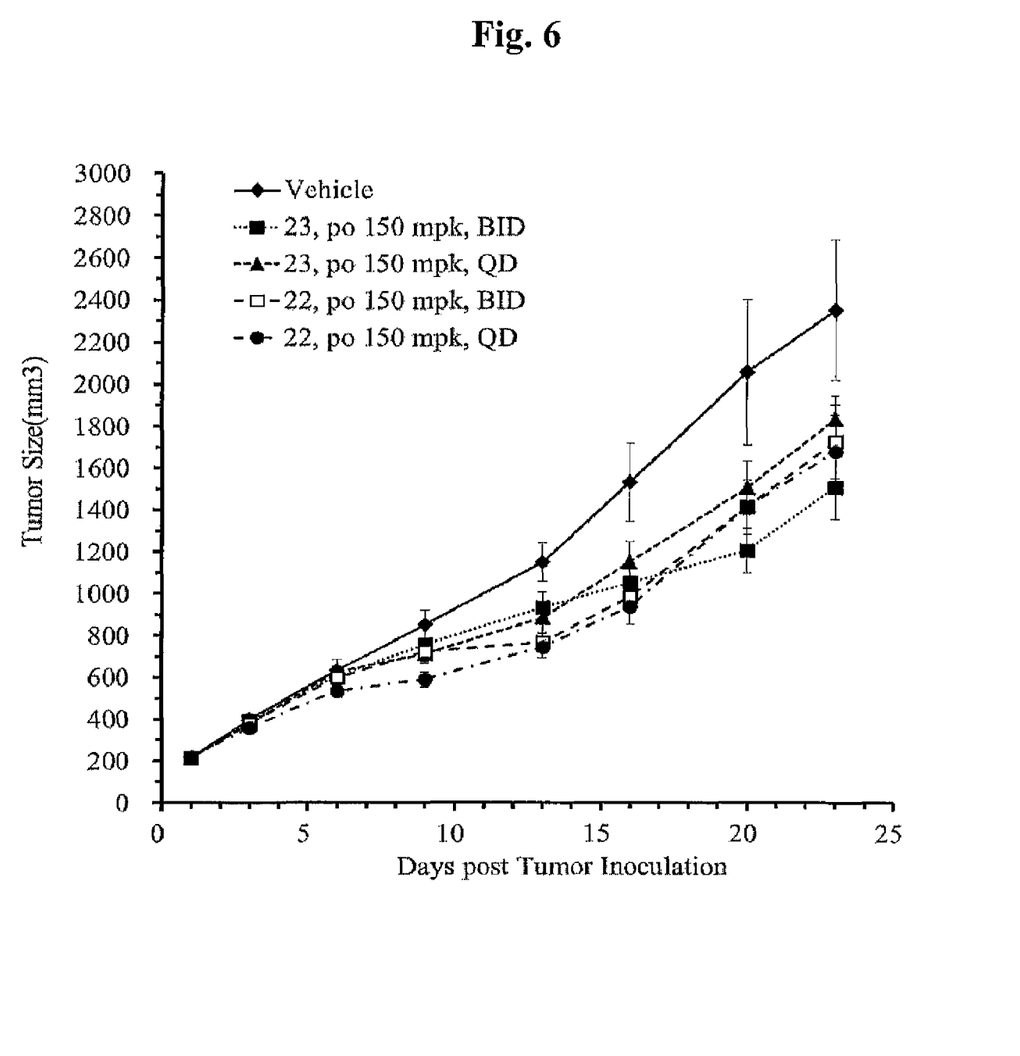
FIG. 6: Tumor growth inhibition (TGI) activities of the Compounds 22 and 23 of Examples 3 and 4.

As shown in FIG. 6, mutual prodrugs (Compounds 22 and 23) exhibit significant anti-cancer activities (40% TGI), while zebularine exhibits marginal activity (10% TGI).

What is claimed is:

1. A compound consisting of a nucleoside of Formula (I) or (II) covalently linked to one or more short chain fatty acids (SCFAs) or a derivative thereof, wherein the SCFAs are selected from the group consisting of butyric acid and isobutyric acid, and the SCFAs are linked at 5' position, or 2', 3', and 5' positions of the nucleoside of formula (I) or (II):

(I)

(II)

2. The compound of claim 1, which is selected from the group consisting of:
   1) ((2R,3S,4S,5R)-5-(4-amino-2-oxopyrimidin-1(2H)-yl)-5-cyano-3,4-dihydroxytetrahydrofuran-2-yl)methyl butyrate;
   2) ((2R,3S,4R,5R)-3,4-dihydroxy-5-(2-oxopyrimidin-1(2H)-yl)tetrahydrofuran-2-yl)methyl butyrate;
   3) (2R,3R,4R,5R)-2-((butyryloxy)methyl)-5-(2-oxopyrimidin-1(2H)-yl)tetrahydrofuran-3,4-diyl dibutyrate; and
   4) (2R,3R,4R,5R)-2-((isobutyryloxy)methyl)-5-(2-oxopyrimidin-1(2H)-yl)tetrahydrofuran-3,4-diyl bis(2-methylpropanoate).

3. A pharmaceutical composition comprising the compound of claim 1, and a pharmaceutically acceptable carrier or an excipient.

4. A method for inhibiting the growth of a cancer cell in a subject, which comprises administering a therapeutically effective amount of the compound of claim 1 to the subject in need thereof.

5. A method for treating a disease, disorder, or condition modulated by an anti-cancer nucleoside and histone deacetylase inhibitor in a subject, which comprises administering a therapeutically effective amount of the compound of claim 1 to the subject in need thereof.

6. The method of claim 5, wherein the disease, disorder, or condition is selected from the group consisting of an autoimmune disease, epithelial tumors, melanoma, leukemia, acute promyelocytic leukemia, lymphoma, osteogenic sarcoma, colon cancer, pancreatic cancer, breast cancer, prostate cancer, ovarian cancer, lung cancer and a combination thereof.

* * * * *